(12) United States Patent
Berben (10) Patent No.: US 9,388,966 B2
(45) Date of Patent: Jul. 12, 2016

(54) WAVELENGTH CONVERSION THROUGH REMOTE PHOSPHOR ON A SUPPORT WHEEL

(75) Inventor: Dirk Berben, Herdecke (DE)

(73) Assignee: OSRAM GMBH, Munich (DE)

( * ) Notice: Subject to any disclaimer, the term of this patent is extended or adjusted under 35 U.S.C. 154(b) by 134 days.

(21) Appl. No.: 14/123,963

(22) PCT Filed: Jun. 9, 2011

(86) PCT No.: PCT/EP2011/059634
§ 371 (c)(1),
(2), (4) Date: Dec. 5, 2013

(87) PCT Pub. No.: WO2012/167831
PCT Pub. Date: Dec. 13, 2012

(65) Prior Publication Data
US 2014/0092581 A1    Apr. 3, 2014

(51) Int. Cl.
*F21V 14/08* (2006.01)
*F21S 10/00* (2006.01)
*F21S 10/02* (2006.01)
*F21V 9/10* (2006.01)
*F21V 9/16* (2006.01)
*A61B 1/06* (2006.01)
*F21S 8/10* (2006.01)
*F21K 99/00* (2016.01)
*F21W 101/00* (2006.01)
*F21Y 101/02* (2006.01)

(52) U.S. Cl.
CPC ............... *F21V 14/08* (2013.01); *A61B 1/0646* (2013.01); *A61B 1/0653* (2013.01); *A61B 1/0669* (2013.01); *F21S 10/007* (2013.01); *F21S 10/02* (2013.01); *F21S 48/1145* (2013.01); *F21S 48/1225* (2013.01); *F21S 48/1721* (2013.01); *F21V 9/10* (2013.01); *F21V 9/16* (2013.01); *F21K 9/56* (2013.01); *F21W 2101/00* (2013.01); *F21Y 2101/02* (2013.01); *F21Y 2101/025* (2013.01)

(58) Field of Classification Search
CPC ......... F21S 48/1721; F21V 14/08; F21K 9/56
See application file for complete search history.

(56) References Cited

U.S. PATENT DOCUMENTS

2009/0103293 A1    4/2009   Herbers et al.
2009/0284148 A1    11/2009  Iwanaga
(Continued)

FOREIGN PATENT DOCUMENTS

CN    102072463 A    5/2011
JP    4054594 B2     2/2008
(Continued)

OTHER PUBLICATIONS

English language abstract of JP 2008052070 A of Mar. 6, 2008.
(Continued)

*Primary Examiner* — Elmito Breval
(74) *Attorney, Agent, or Firm* — Viering, Jentschura & Partner mbB (57) ABSTRACT

A lighting device may include at least one phosphor region which can be irradiated by a primary light source, and at least one optical filter region which can be disposed downstream of the at least one phosphor region, wherein the at least one phosphor region and the at least one filter region are arranged at a different level on a common support wheel.

14 Claims, 8 Drawing Sheets

(56) References Cited

U.S. PATENT DOCUMENTS

2011/0116253 A1   5/2011  Sugiyama
2012/0068630 A1   3/2012  Li et al.
2012/0230013 A1   9/2012  Xu

FOREIGN PATENT DOCUMENTS

| | | |
|---|---|---|
| JP | 2008052070 A | 3/2008 |
| JP | 4354435 B2 | 10/2009 |
| WO | 2006133214 A2 | 12/2006 |
| WO | 2009017992 A1 | 2/2009 |
| WO | 2010133090 A1 | 11/2010 |

OTHER PUBLICATIONS

English abstract of JP 4054594 B2 of Feb. 27, 2008.

English abstract of JP4354435 B2 of Oct. 28, 2009.

Office Action issued in the corresponding Chinese application No. 201180071523.X, dated Jun. 5, 2014.

WAVELENGTH CONVERSION THROUGH REMOTE PHOSPHOR ON A SUPPORT WHEEL

RELATED APPLICATIONS

This application is a national stage entry according to 35 U.S.C. §371 of PCT application No.: PCT/EP2011/059634 filed on Jun. 9, 2011.

TECHNICAL FIELD

Various embodiments relate to a lighting device, including at least one phosphor region which can be irradiated by a primary light source, and at least one optical filter region which can be disposed downstream of the at least one phosphor region, wherein the at least one phosphor region is arranged on a rotatable support wheel and the at least one filter region is also arranged on a rotatable support wheel. The present disclosure is particularly advantageously applicable to vehicles, in particular to motor vehicles, in particular to vehicle headlights. The present disclosure is also advantageously applicable in general lighting and for medical purposes, e.g. as endoscopy lighting.

BACKGROUND

In the case of a lighting device of the type described in the introduction, a primary light can be generated by means of the primary light source. During operation of the lighting device, said primary light hitherto has impinged on a disk-shaped, rotating first support wheel having a plurality of different phosphor regions. The different phosphor regions generate differently wavelength-converted light (that is to say light of different colors or different spectral compositions). As a result of the rotation of the support wheel, the phosphor regions are successively activated and a temporally serial sequence of differently colored secondary light sections is thus generated. The phosphor regions are typically arranged in an annular fashion on the first support wheel and form sectors thereof.

However, the primary light currently incident on a phosphor region is typically not completely converted, and so the secondary light emitted by said phosphor region includes both a (usually dominant) wavelength-converted light component and an undesired non-wavelength-converted primary light component. In order to be able to output a substantially pure wavelength-converted light component, an associated filter region is disposed downstream of such a phosphor region and filters out the primary light component of the secondary light. Depending on the type of wavelength-converted light and the proportion thereof in the secondary light, a different filter region can be used in order to optimize an efficiency of the lighting device. In order to be able to provide a filter region matching a phosphor region, the filter regions are arranged in an annular fashion on a circular-disk-shaped second support wheel. The second support wheel has to be operated synchronously with the first support wheel in order to be able to maintain a high efficiency and to avoid color corruption as a result of non-matching combinations of phosphor regions and filter regions.

The output light beam present downstream of the second support wheel is temporally serially composed analogously to the secondary light, wherein the individual (temporally serial) sections thereof in each case correspond to a predetermined combination of a currently active phosphor region and an associated filter region. The relative duration of the sections can be set via the length of the phosphor regions (and thus the corresponding length of the associated filter region). If the sequence of the sections occurs rapidly enough, the individual sections are no longer resolved by a human observer, and the output light beam is perceived as a uniform mixed light. The individual sections act as different color components of the mixed light.

The support wheels are typically angled with respect to one another and have to be precisely synchronized, which necessitates a considerable constructional outlay, e.g. owing to the use of high-quality and thus expensive drive motors for the support wheels and on account of complex synchronization control. A probability of failure of the support wheels is also comparatively high.

SUMMARY

Various embodiments provide a lighting device of the type mentioned in the introduction which at least partly eliminates the disadvantages of the prior art and in particular is more precisely synchronized and less expensive.

Various embodiments provide a lighting device, including at least one phosphor region which can be irradiated by a primary light source, and including at least one optical filter region which can be disposed downstream of the at least one phosphor region, wherein the at least one phosphor region and the at least one filter region are arranged at a different level on a common support wheel.

The lighting device may be, in principle, a lamp, a module or a luminaire.

The primary light source generates primary light. The primary light may be in particular substantially light having only one wavelength or one peak wavelength and a narrow bandwidth. The narrowband or monochromatic primary light can be generated directly, e.g. by means of at least one laser, including a solid-state laser or a dye laser, and/or by means of at least one light emitting diode. Alternatively, the primary light source may generate the light e.g. in a broadband fashion and then filter it. However, the primary light may also be broadband or have a plurality of spectral bands.

A phosphor region may be understood to mean, in particular, a region including at least one phosphor. A phosphor may in particular be able to convert primary light incident on it at least partly into light having at least one other, in particular longer, wavelength ("down-converting"). A phosphor remote or at a distance from the primary light source is often also designated as "remote phosphor".

An optical filter region can be understood to mean, in particular, a region which filters light passing through it in a spectrally defined manner, e.g. filters out a predetermined spectral band from the light passing through or leaves only a predetermined spectral band in the light passing through.

By virtue of the fact that the at least one phosphor region and the at least one filter region are now arranged on the same support wheel, an active synchronization is obviated, and associated phosphor regions and filter regions are unalterably aligned with one another and thus fixedly synchronized. Moreover, only one support wheel is required, which increases fail-safety and considerably reduces costs. Furthermore, a less expensive drive motor can be used for driving the only one common (rotatable) support wheel. As a result of the arrangement of the at least one phosphor region, on the one hand, and the at least one filter region, on the other hand, at different levels (in particular in a spaced apart manner with respect to a longitudinal extension along the axis of rotation), an optical accessibility of the at least one phosphor region is simplified (particularly when the primary light is incident obliquely with respect to the axis of rotation) and a compact design is also supported.

In one configuration, the at least one phosphor region is arranged on a first rotational ring region of the support wheel, and the at least one filter region is arranged on a second rotational ring region of the support wheel. The rotational ring regions are thus likewise arranged at a different level with respect to an axis of rotation of the support wheel. A rotational ring region of a rotatable support wheel can be understood to mean, in particular, a projection region on the support wheel which arises when the support wheel is rotated under a spatially fixed light beam. During rotation of the support wheel, the spatially fixed light beam thus sweeps over the projection ring region or writes a track in the projection ring region. The first rotational ring region is, in particular, that region in which a focal spot generated by the primary light or the primary light beam is situated. The second rotational ring region is, in particular, that region in which a focal spot generated by the secondary light or the secondary light beam is situated.

In particular, the first rotational ring region and the second rotational ring region may also have other regions.

Thus, in yet another configuration, the first rotational ring region has at least one phosphor region and at least one reflection region, wherein the reflection region is designed to reflect at least a primary light that can be emitted by the primary light source. As a result, the primary light as such can also be used as a serial section of an output light beam of the lighting device, in particular as a color component of a mixed light. The reflection region can be a specularly or diffusely reflective region.

Moreover, in another configuration, the second rotational ring region has at least one filter region and at least one non-filtering region. The non-filtering region is able, in particular, to transmit a reflection light reflected by the reflection region for the primary light. This brings about an efficient and readily controllable utilization of the primary light. The reflection region and the region that does not filter the primary light can therefore be associated regions which are irradiated simultaneously or in a common optical path. The non-filtering region may be a transparent or a translucent or diffusely scattering region.

In one possible configuration, the first rotational ring region has a single phosphor region including a plurality of different, mixed phosphors. In this regard, a secondary light is generated which has a plurality of converted wavelengths and the residual primary light component. The second rotational ring region may then have, in particular, a plurality of filter regions in order to filter out the desired wavelength ranges from the secondary light. A relative duration of the thus filtered serial sections of the output light beam downstream of the support wheel or the filter regions may be set by a length of the filter regions.

In a further possible configuration, the first rotational ring region has a plurality of phosphor regions each including different phosphors. In this regard, a secondary light is generated which typically has a converted wavelength and the residual primary light component. The second rotational ring region may then have an identical filter region for all the phosphor regions in order to filter out the respective primary light component. A relative duration of the thus filtered serial sections of the output light beam downstream of the support wheel can be set by a length of the phosphor regions and a corresponding length of the associated filter regions.

In each of the configurations, the first rotational ring region can have at least one reflection region and the second rotational ring region can have at least one associated region which does not filter at least the primary light.

For setting a cumulative color locus of a (serial) mixed light output by the lighting device in a large range ("gamut"), it is preferred for the primary light to be a UV light or blue light.

The blue light preferably has a wavelength or peak wavelength of between 405 nm and 485 nm.

Particularly for the case where the primary light is UV light, the lighting device can have at least three phosphor regions on the first rotational ring region, the phosphors of which convert the primary UV light e.g. into red, green and blue light, respectively. A common UV filter can be disposed downstream of the three phosphor regions e.g. on the second rotational ring region. The first rotational ring region then preferably has no reflection region.

For the case where the primary light is blue light (e.g. having a peak wavelength of 485 nm), the lighting device may have at least two phosphor regions on the first rotational ring region, the phosphors of which convert the primary blue light e.g. into red and green light. A common blue light filter, for example, may be disposed downstream of the two phosphor regions. The first rotational ring region, for providing a blue color component of the mixed light, may preferably have a reflection region for the blue primary light, which is assigned a non-filtering region on the second rotational ring region.

For the case where the primary light is blue light (e.g. having a peak wavelength of 445 nm), for example, the lighting device can have at least three phosphor regions on the first rotational ring region, the phosphors of which convert the primary blue light e.g. into blue light having a higher wavelength (e.g. 465 nm), into red light and into green light, respectively. A blue light filter for the blue primary light of 445 nm, for example, may be disposed downstream of the blue-blue converting phosphor region. A less expensive blue light filter for blue light including the wavelength range of between 465 nm and 485 nm, for example, may be disposed downstream of the blue-red converting and blue-green converting phosphor regions. The first rotational ring region preferably has no reflection region.

In another configuration, at least the at least one phosphor region and the at least one filter region are angled relative to one another. In particular, the rotational ring regions may also be angled relative to one anther. As a result, a luminous spot on each of the rotational ring regions can be kept small, particularly when the primary light beam is incident obliquely, which reduces a material outlay and fosters a compact design.

In one configuration, the support wheel has a base and a circumferential wall rising from the base, wherein the at least one phosphor region is formed on the wall and the at least one filter region is formed on the base. It is thus possible to provide a support wheel which is producible in a simple manner (without an undercut) and is rotatable without an unbalance.

In one specific development, the first rotational ring region (which apart from the at least one phosphor region can e.g. also have a reflection region) is formed on the wall and the second rotational ring region (which apart from the at least one filter region can e.g. also have a non-filtering light transmission region) is formed on the base.

In one configuration, moreover, the support wheel is formed in a cup-shaped fashion and the wall is an outer wall adjacent to an edge of the base.

In an alternative configuration, the wall is an inner wall rising from a central region of the base.

In one configuration, moreover, the base is formed substantially in a planar fashion and/or the wall is formed rectilinearly in profile. This basic form can be produced in a simple manner and can be occupied by a phosphor region and/or a filter region.

Alternatively or additionally, the base and/or the wall may be formed in a curved fashion in profile. This basic form may be produced in a particularly simple manner and may be occupied by a phosphor region and/or a filter region.

In yet another configuration, the support wheel is formed at least partly in a strut-shaped fashion. The support wheel may thus be configured in a particularly lightweight fashion, without significantly losing stability. The struts may form a honeycomb-shaped supporting framework. The struts may be present in particular on a wall of the support wheel, and thus enable a primary beam radiating through the wall with only little shading. This may be advantageous particularly in the case of a support wheel which surrounds a reflector to an extent such that the support wheel is arranged between the primary light source and a passage region of the reflector for the primary light.

In one configuration, in addition, an associated combination of a phosphor region and a filter region are arranged in a circle sector that is identical with respect to the axis of rotation. Particularly simple beam guiding of the secondary light can thus be implemented. In one configuration, furthermore, the lighting device has a reflector arranged at least partly between the primary light source and the phosphor region which can be irradiated by the primary light source, wherein the reflector is at least partly transmissive to a primary light that can be emitted by the primary light source and is at least partly reflective to a light emitted by the phosphor region, and wherein the at least one optical filter region can be disposed downstream of the reflector. The reflector may therefore direct, in particular focus, light emitted by a region situated on the first rotational ring region and currently illuminated by the primary light up to an associated region on the second rotational ring region. Such a reflector enables a particularly compact design.

The reflector may be, in particular, a shell-shaped reflector. The reflector may, in particular, curve over the phosphor region currently irradiated by the primary light.

The transmission of the primary light beam through the reflector may be achieved through a transmission region in particular in the form of a transparent window in the reflector. In this case, particularly with a small area of the window, it is accepted that secondary light incident on the window can emerge again from the window and is lost. Alternatively, the window can be a window that is transmissive to the primary light, but not transmissive to wavelength-converted light. In this regard, only primary light not converted by the phosphor region is lost, which reduces its disturbing proportion at the associated filter region.

In one development, moreover, the reflector is surrounded at least partly by the support wheel, in particular the cup-shaped support wheel. This enables a particularly compact design. In particular, the support wheel may surround the reflector to an extent such that the support wheel is arranged between the primary light source and a passage region of the reflector for the primary light. The support wheel is then advantageously at least locally transmissive to the primary light beam that can be generated between the primary light source and the reflector. The transmissivity may be achieved e.g. by means of a strut construction or through a substantially ring-shaped transmission window.

In another configuration, the light source is a semiconductor light source, in particular a light emitting diode or a laser light source. It is thus possible to provide a compact and long-lived light source having a high radiant power and a well-defined wavelength of the primary light. For this purpose, the laser light source can be, in particular, a semiconductor laser or a laser diode.

In one configuration, furthermore, the lighting device is a vehicle lighting device. A compact and long-lived vehicle lighting device is provided as a result. The vehicle may be in particular a motor vehicle, but also an aircraft, a ship, etc. The vehicle lighting device may be configured, in particular, as a headlight or as a part thereof.

BRIEF DESCRIPTION OF THE DRAWINGS

In the drawings, like reference characters generally refer to the same parts throughout the different views. The drawings are not necessarily to scale, emphasis instead generally being replaced upon illustrating the principles of the disclosure. In the following description, various embodiments of the disclosure are described with reference to the following drawings, in which.

DETAILED DESCRIPTION

The following detailed description refers to the accompanying drawings that show, by way of illustration, specific details and embodiments in which the disclosure may be practiced.

Figure 1:
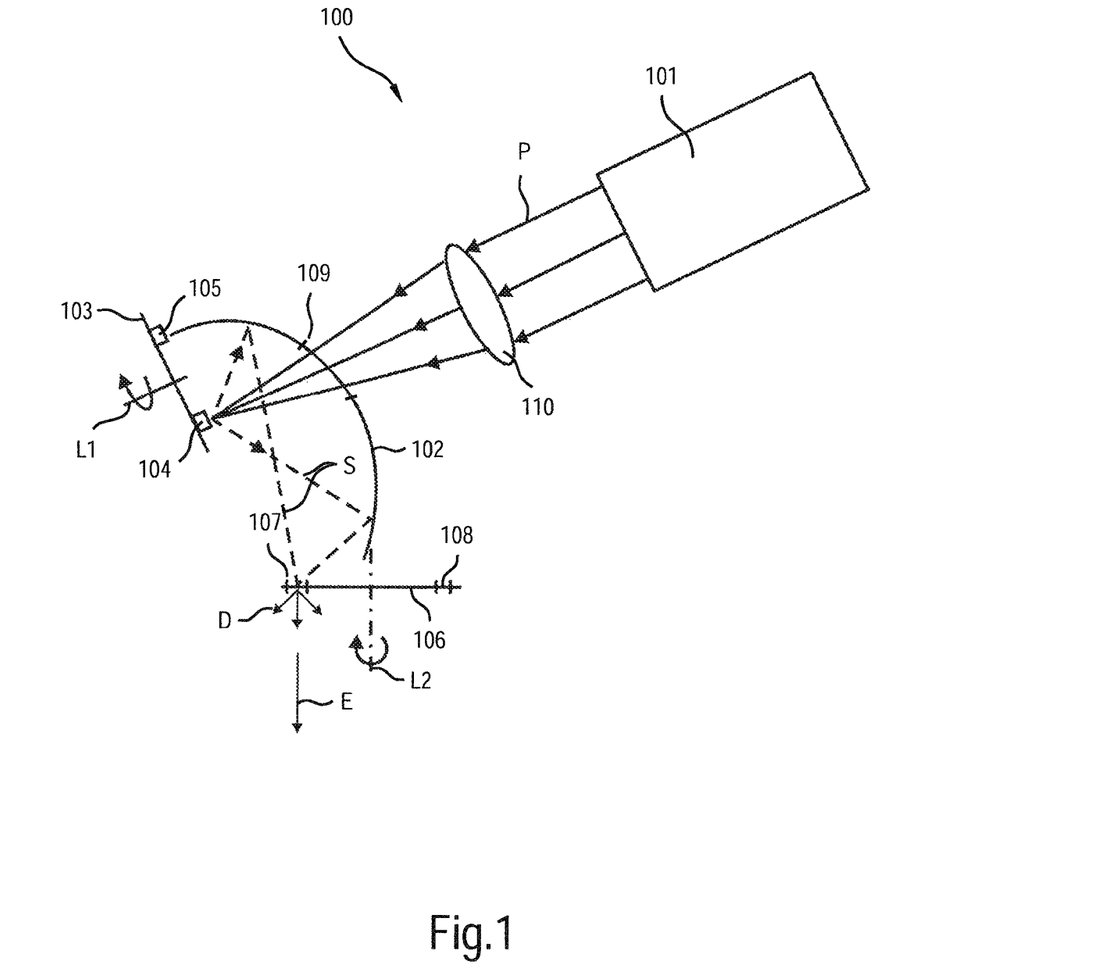
FIG. 1 shows a lighting device including a plurality of support wheels as a sectional illustration in side view.

FIG. 1 shows a lighting device 100 including a primary light source in the form of a semiconductor laser 101, a shell-shaped reflector 102, a first support wheel 103 having a phosphor region 104 and a reflection region 105, and including a second support wheel 106 having a filter region 107 and a non-filtering light transmission region 108.

The semiconductor laser 101 emits blue primary light P, to be precise obliquely, i.e. in a direction angled with respect to a main emission direction E of an output light beam D emerging from the second support wheel 106. A flexibly arrangeable, in particular narrow arrangement of the lighting device 100 can thus be achieved.

In a first rotary position shown, the semiconductor laser 101 irradiates an outer side of the reflector 102, to be precise in a region in which a window 109 is situated, said window being transmissive to the primary light P. The primary light P emerging from the semiconductor laser 101 thus radiates through the reflector 102 onto the phosphor region 104, to be precise in a manner focused by a lens 110 disposed downstream of the semiconductor laser 101.

The phosphor region 104 includes here, purely by way of example, two phosphors in a predefined mixture, namely a blue-red converting phosphor and a blue-green converting phosphor. Since the mixture of the phosphors is readily adjustable, the associated light proportions of the light emitted by the phosphor region 104 are also readily adjustable. However, a fraction of the blue primary light P incident on the phosphor region 104 is not wavelength-converted, but rather emitted diffusely. A precise adjustment of the disturbing primary light component can be carried out only with difficulty or with increased outlay. The secondary light S emitted by the phosphor region 104 thus has a red color component, a green color component and a blue color component.

The secondary light S is deflected onto the filter region 107 at least partly (e.g. in a manner attenuated slightly on account of a loss through the window 109) by the reflector 102 curving over the phosphor region 104. The filter region 107 filters out the component of the primary light P from the secondary light S, but transmits the red and green light components. The output light beam D thus filtered may be shaped further (in particular straightened or parallelized), e.g. by means of a downstream lens or a light rod (not illustrated).

In the second rotary position, the first support wheel 103 and the second support wheel 106 have been rotated synchronously about their axes L1 and respectively L2 of rotation (as indicated by the curved arrows) to an extent such that now the reflection region 105 is irradiated by the primary light P and the light transmission region 108 is irradiated by the secondary light S. In this second rotary position, therefore, the primary light P is reflected firstly by the reflection region 105 and then by the reflector 102 and subsequently transmitted through the light transmission region 108.

During a synchronous rotation of the support wheels 103 and 106 at the same rotational speed, therefore, an output light beam D is generated which has serially a red-green section and a blue section. At a sufficiently high rotational speed, this is perceived as a red-green-blue mixed light.

The support wheels 103 and 106 have to be precisely synchronized in order to avoid chromatic aberrations, which necessitates a considerable constructional outlay, e.g. through the use of high-quality and thus expensive drive motors and on account of complex synchronization control. Moreover, a probability of failure of the support wheels 103 and 106 is comparatively high.

Figure 2:
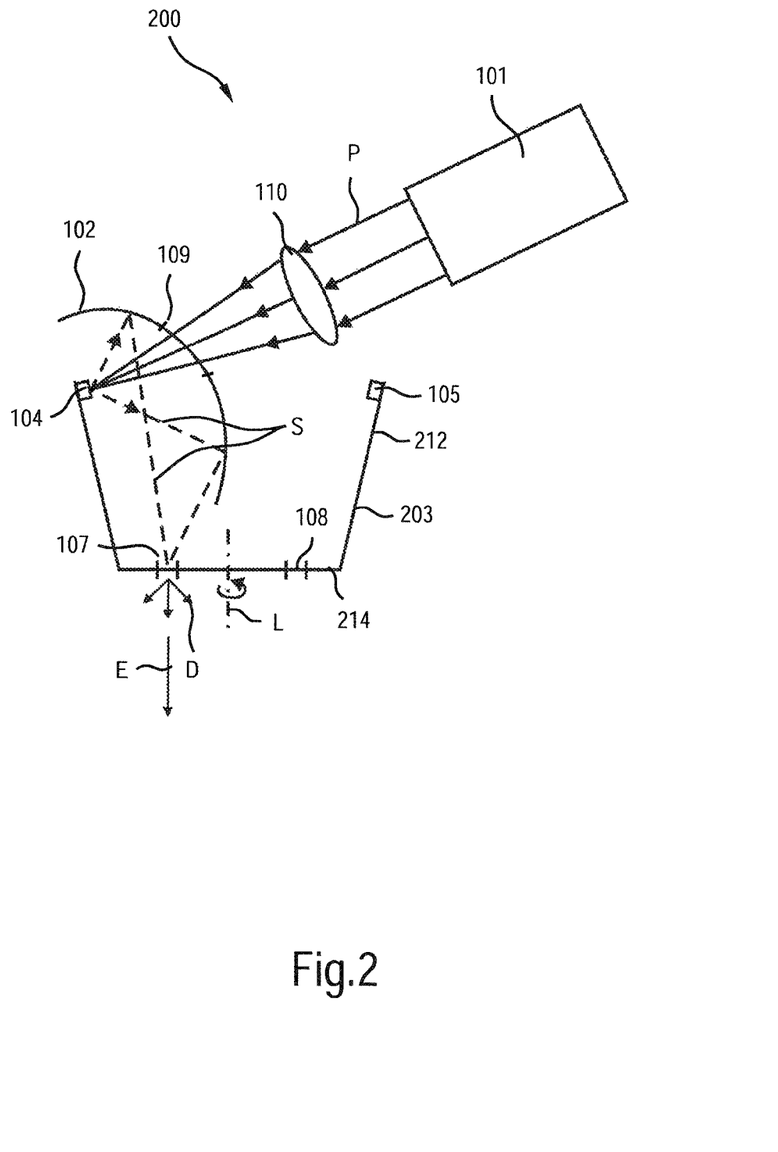
FIG. 2 shows a lighting device according to the disclosure including a common support wheel in accordance with a first embodiment as a sectional illustration in side view.
Figure 3:
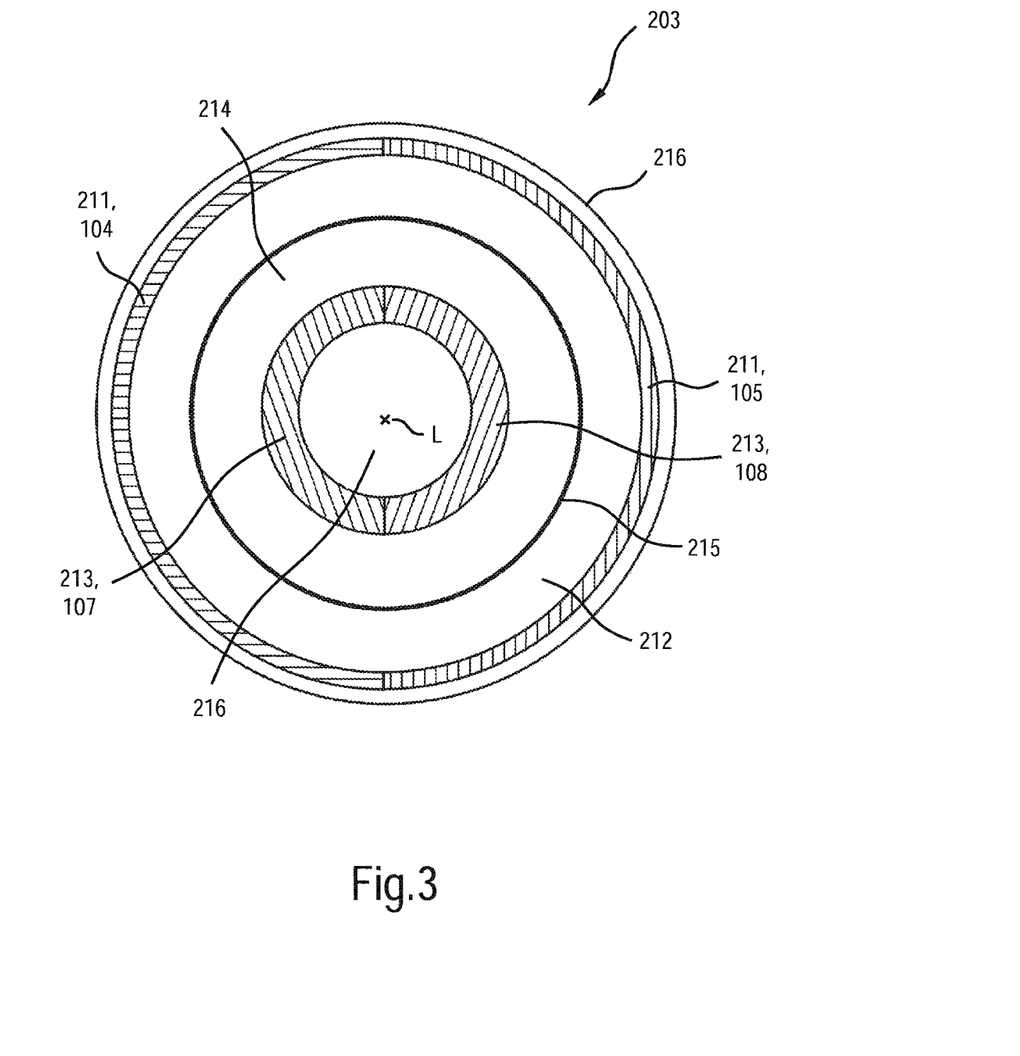
FIG. 3 shows the common support wheel in plan view.
Figure 4:
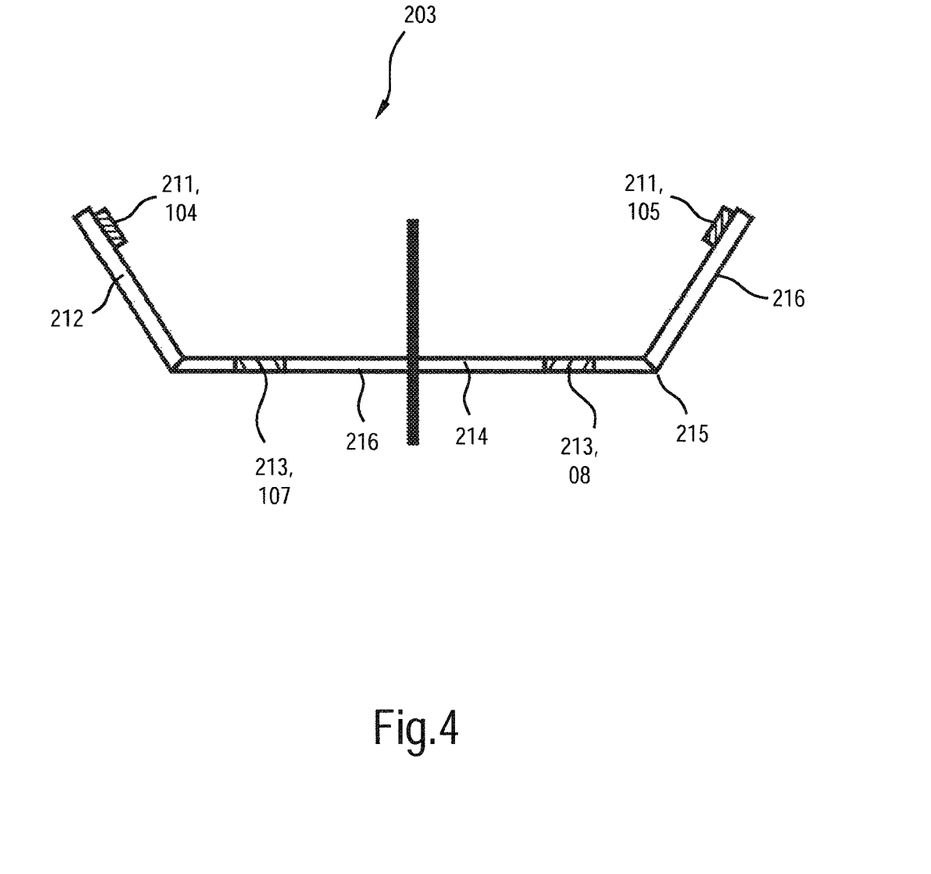
FIG. 4 shows the common support wheel as a sectional illustration in side view.

FIG. 2 shows a lighting device 200 including a common, cup-shaped support wheel 203 as a sectional illustration in side view. The light device 200 differs from the lighting device 100 in that two support wheels are no longer used now, rather use is made of the common support wheel 203 for the phosphor region 104, the reflection region 105, the filter region 107 and the light transmission region 108. FIG. 3 shows the common support wheel 203 in plan view. FIG. 4 shows the common support wheel 203 as a sectional illustration in side view.

In the case of the lighting device 200, therefore, only the common support wheel 203 need be rotated. As a result, an active synchronization is obviated, and the regions 104, 105, 107 and 108 are unalterably aligned with one another and thus fixedly synchronized. Moreover, as a result of the only one support wheel 203, fail-safety is increased and costs are reduced. Furthermore, a less expensive drive motor may be used for driving the support wheel 203.

As a result of an arrangement of the regions 104 and 105 (which form a first, annular rotational ring region 211), on the one hand, and the regions 107 and 108 (which form a second, annular rotational ring region 213), on the other hand, at different levels (in a spaced apart manner with respect to a longitudinal extension along the axis L of rotation), the position of the simultaneously active regions 104 and 107 and respectively 105 and 108 is maintained, such that the operation of the lighting device 200 is analogous to the already described operation of the lighting device 100. In particular, an accessibility of the regions 104 and 105 for the incident primary light P obliquely with respect to the axis L of rotation and also a compact design are thus maintained.

The regions 104 and 105 form a first, annular rotational ring region 211 on a wall 212 of the support wheel 203. During a rotation of the support wheel 203, the luminous spot of the primary light beam remains within the first rotational ring region 211 and moves over the latter in a manner brought about by the rotation of the support wheel 203. The regions 107 and 108 form a second, annular rotational ring region 213 on a base 214 of the support wheel 203. During a rotation of the support wheel 203, the luminous spot of the secondary light beam remains within the second rotational ring region 213 and moves over the latter in a manner brought about by the rotation of the support wheel 203.

The wall 212, as shown in FIG. 4, is formed in a rectilinear fashion in profile. The base 214 is formed in a planar fashion, the (circumferential) wall 212 projecting obliquely from a circumferential edge 215 of the base 214. The first rotational ring region 211 is thus angled with respect to the second rotational ring region 213. Consequently, the regions 104 and 105 are also angled with respect to the regions 107 and 108, respectively.

A main body 216 of the support wheel 203 is formed in a whole-area fashion here.

As shown in FIG. 4, in particular, an associated combination of a phosphor region 104 and a filter region 107 and respectively a reflection region 105 and a non-filtering region 108 are arranged in a circle sector of here 180° that is identical with respect to the axis L of rotation.

Figure 5:
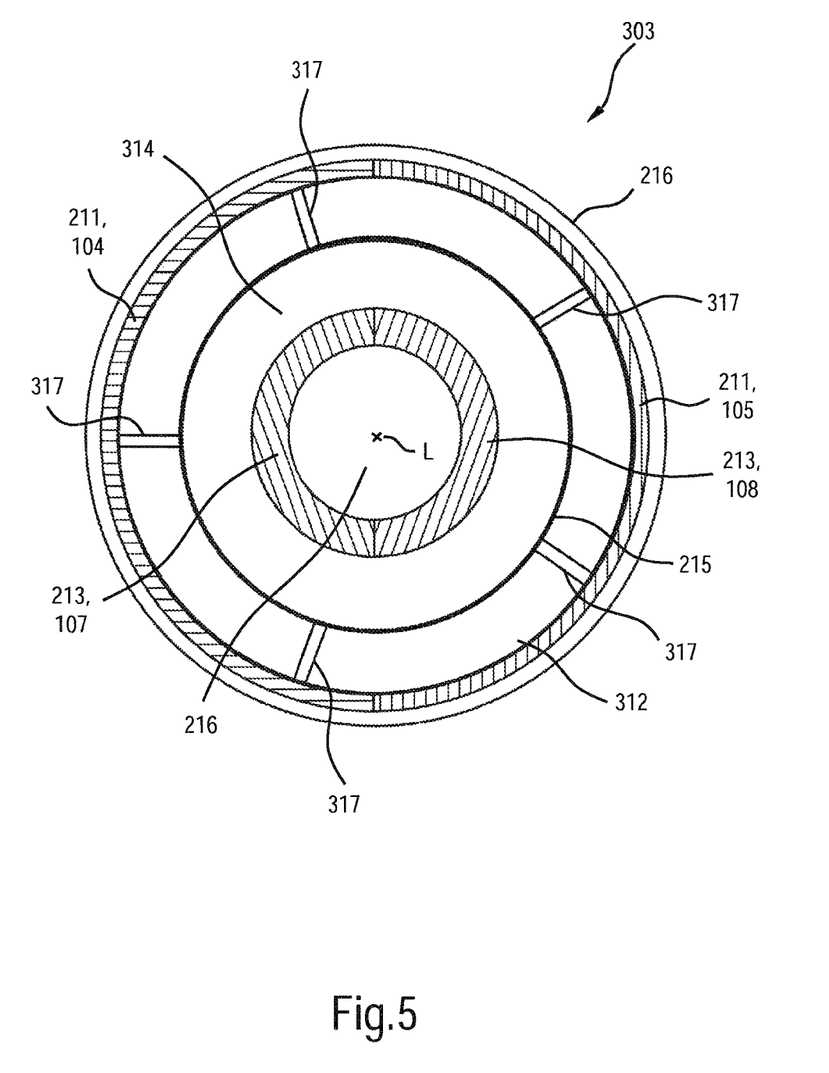
FIG. 5 shows a common support wheel in accordance with a second embodiment in plan view.

FIG. 5 shows a common support wheel 303 in accordance with a second embodiment in plan view. The support wheel 303 differs from the support wheel 203 in that a wall 312 between the edge 215 and the first rotational ring region 211 is formed in a strut-shaped fashion.

Five spokes or struts 317 extending radially with respect to the axis L of rotation are provided here for this purpose. The width of the struts 317 may be approximately 1 mm, for example, and a diameter of the first rotational ring region 211 can be approximately 40 nm. In this regard, the support wheel 303 may also be operated in a manner inclined even further than is shown in FIG. 2. In particular, as also shown analogously in the subsequent FIG. 6, the support wheel 303 may then surround the reflector 102 to an extent such that the support wheel 303 is arranged between the semiconductor laser 101 and the window 109 of the reflector 102. On account of the struts 317 the support wheel 303 is substantially transmissive, or transmissive with only a low loss, to the beam of the primary light P that may be generated between the semiconductor laser 101 and the reflector 102.

At a rotational speed of the support wheel 303 of approximately 7200 rpm and with a diameter of the primary light P at the location of the wall 312 of approximately 15 mm, a loss of light through the struts 317 is only approximately 0.3%, but enables a particularly compact design.

Figure 6:
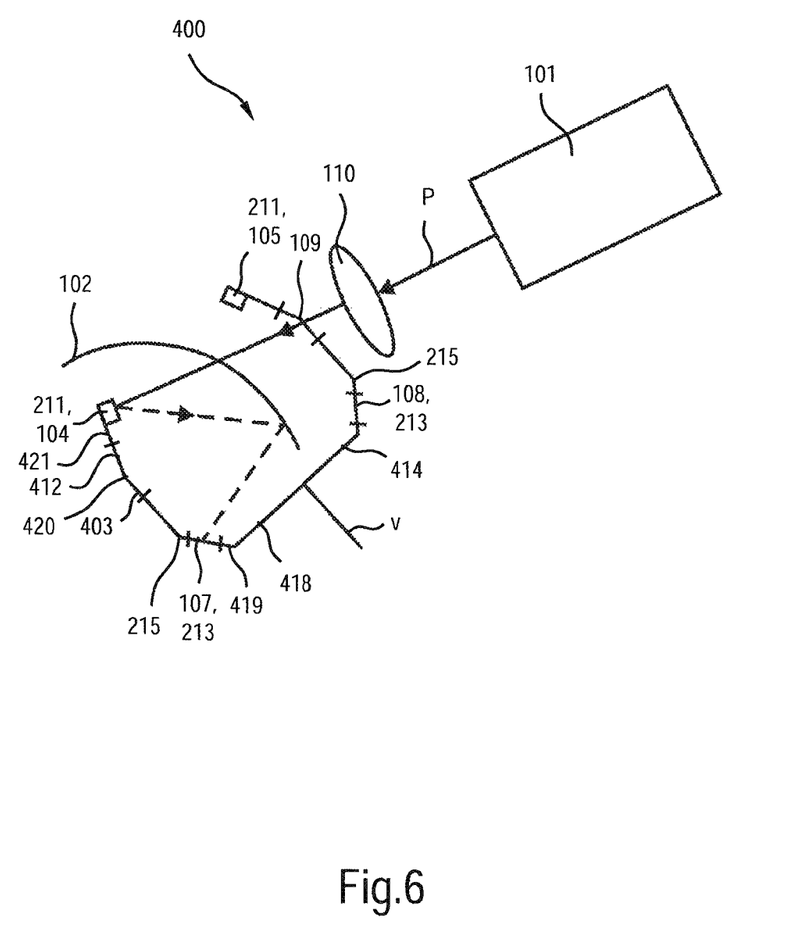
FIG. 6 shows a lighting device according to the disclosure including a common support wheel in accordance with a third embodiment as a sectional illustration in side view.

FIG. 6 shows a lighting device 400 according to the disclosure including a common support wheel 403 in accordance with a third embodiment as a sectional illustration in side view. The lighting device 400 is constructed similarly to the lighting device 200, the support wheel 403 now being used.

The support wheel 403 has an axis L of rotation which is inclined further in the direction of the semiconductor laser 101 and here is no longer perpendicular. In order nevertheless to maintain at least approximately the position and spatial situation of the regions 104, 105, 107 and 108 as in the case of the lighting device 200, both the base 414 and the outer wall 412 are configured in a manner curved inward. For this purpose, the base 414 has in profile a curvature like a polygon progression with a planar central region 418 and an edge region 419 bent up like a margin. The outer wall 412 likewise has a curvature like a polygon progression in profile, to be precise with a perpendicular wall region 420 adjacent to the edge 215 of the base 414, and with an edge region 421 bent inward like a margin. The first rotational ring region 211 or the regions 104 and 105 are arranged on an inner side of the edge region 421 of the outer wall 412.

This support wheel 403 enables the reflector 102 to be enclosed or accommodated particularly extensively, and thus a compact design. For the transmission of the primary light P from the semiconductor laser 101 to the reflector 102, here as well the outer wall 412 is configured at least partly (outside the second rotational ring region 213), in a strut-like fashion.

Figure 7:
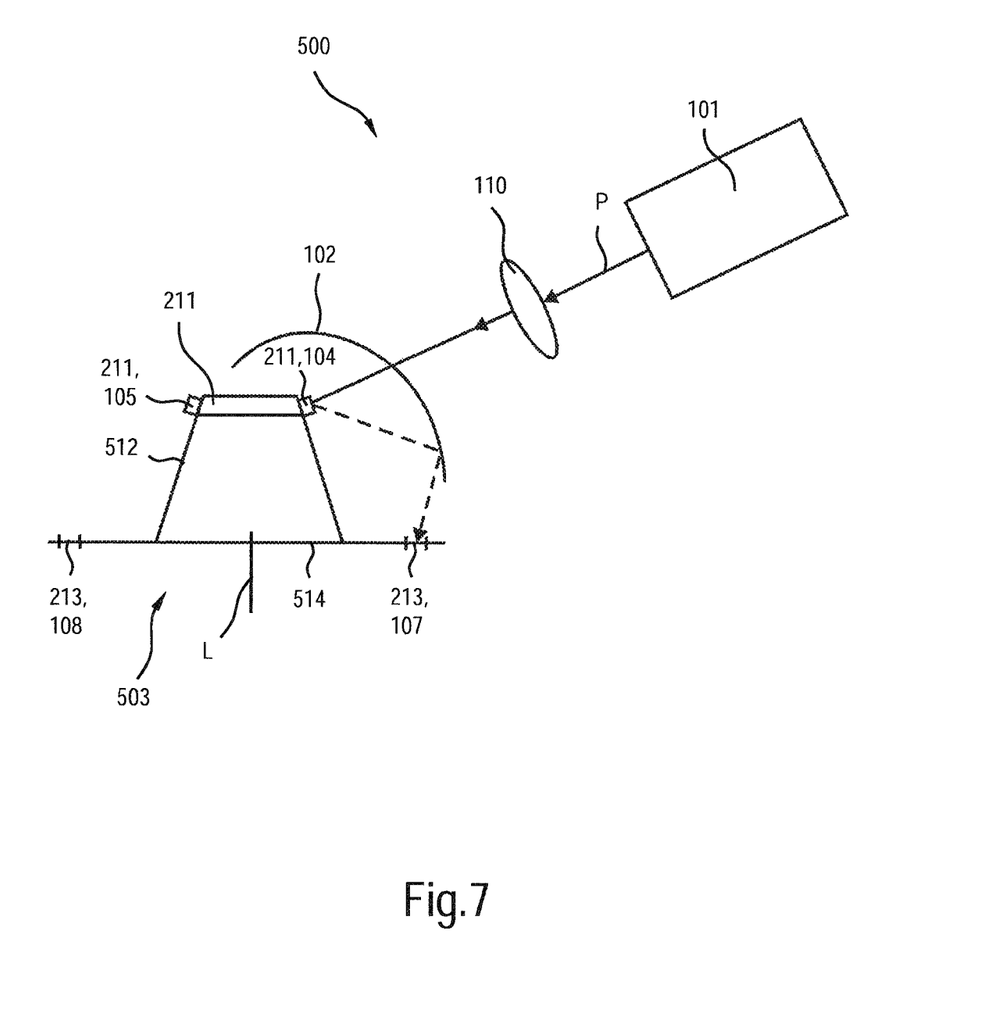
FIG. 7 shows a lighting device according to the disclosure including a common support wheel in accordance with a fourth embodiment as a sectional illustration in side view.

FIG. 7 shows a lighting device 500 according to the disclosure including a common support wheel 503 in accordance with a fourth embodiment as a sectional illustration in side view. The lighting device 500 is constructed similarly to the lighting device 200, the support wheel 503 now being used. In contrast to the support wheels 203, 303 and 403, the support wheel 503 has a circumferential inner wall 512 rising from a central region of the base 514. The inner wall 512 is configured here in the shape of a truncated cone, and the base 514 is planar or rectilinear in profile.

The second rotational end region 213 or the regions 107 and 108 are arranged on the base 514 outside the inner wall 512. The first rotational ring region 211 or the regions 104 and 105 are arranged on an upper (free) end of an outer side (lateral surface) of the inner wall 512. The support wheel 503 can be operated, in particular, in such a way that its axis L of rotation is perpendicular as in the case of the support wheel 203.

Figure 8:
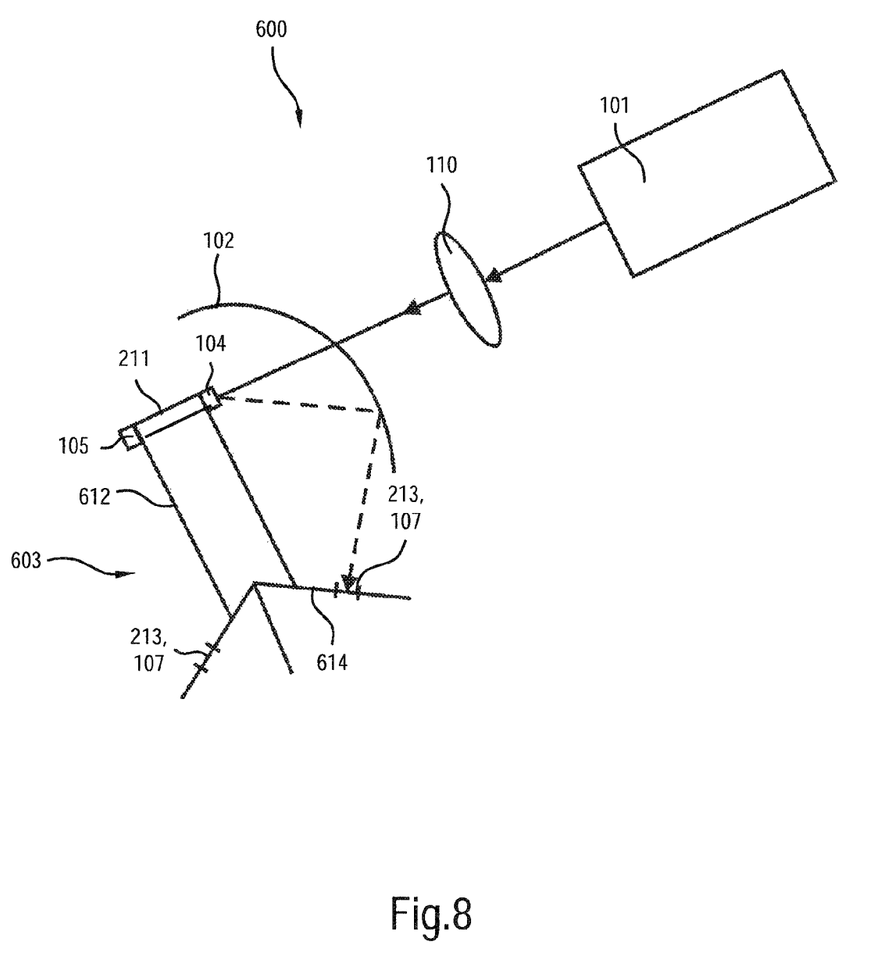
FIG. 8 shows a lighting device according to the disclosure including a common support wheel in accordance with a fifth embodiment as a sectional illustration in side view.

FIG. 8 shows a lighting device 600 according to the disclosure including a common support wheel 603 in accordance with a fifth embodiment as a sectional illustration in side view. The lighting device 600 is constructed similarly to the lighting device 500, the support wheel 603 now being used.

In contrast to the support wheel 503, the support wheel 603 has a non-planar base 614, namely a base 614 that is conical or in the shape of a truncated cone. The inner wall 612 projecting upward centrally therefrom is now formed in a cylindrical fashion. The second rotational ring region 213 or the regions 107 and 108 here as well are arranged on the base 614 outside the inner wall 612. The first rotational ring region 211 or the regions 104 and 105 here as well are arranged on an upper (free) end of an outer side (lateral surface) of the inner wall 612. This support wheel 612 can be operated, in particular, with an obliquely aligned axis L of rotation.

Although the disclosure has been more specifically illustrated and described in detail by means of the exemplary embodiment shown, the disclosure is not restricted thereto, and other variations can be derived therefrom by a person skilled in the art, without departing from the scope of protection of the disclosure.

In this regard, generally it is also possible for there to be more than one phosphor region and/or more than one reflection region on the first rotational ring region. In addition, it is also possible for there to be more than one filter region and/or more than one reflection region on the second rotational end region.

For setting the cumulative color locus even more flexibly, the primary light source may also be switched off for a specific period of time.

The primary light source may additionally include one or a plurality of light emitting diodes and/or laser diodes having the same and/or different wavelength(s).

While the disclosed embodiments have been particularly shown and described with reference to specific embodiments, it should be understood by those skilled in the art that various changes in form and detail may be made therein without departing from the spirit and scope of the disclosed embodiments as defined by the appended claims. The scope of the disclosed embodiments is thus indicated by the appended claims and all changes which come within the meaning and range of equivalency of the claims are therefore intended to be embraced.

LIST OF REFERENCE SIGNS

100 Lighting device
101 Semiconductor laser
102 Reflector
103 First support wheel
104 Phosphor region
105 Reflection region
106 Second support wheel
107 Filter region
108 Light transmission region
109 Window
110 Lens
200 Lighting device
203 Common support wheel
211 First rotational ring region
212 Wall
213 Second rotational ring region
214 Base
215 Edge of the base
216 Main body of the common support wheel
303 Support wheel
312 Wall
317 Strut
400 Lighting device
403 Support wheel
412 Wall
414 Base
415 Edge
418 Central region
419 Edge region
420 Wall region
421 Edge region
500 Lighting device
503 Support wheel
512 Inner wall
514 Base
600 Lighting device
603 Support wheel
612 Inner wall
614 Base
D Output light beam
L Axis of rotation of the common support wheel
L1 Axis of rotation of the first support wheel
L2 Axis of rotation of the second support wheel
E Main emission direction
P Primary light
S Secondary light

The invention claimed is:
1. A lighting device,
comprising at least one phosphor region which can be irradiated by a primary light source, and at least one optical filter region which can be disposed downstream of the at least one phosphor region, wherein the at least one phosphor region and the at least one filter region are arranged at a different level on a common support wheel.

2. The lighting device as claimed in claim 1, wherein the at least one phosphor region is arranged on a first rotational ring region of the support wheel, and the at least one filter region is arranged on a second rotational ring region of the rotatable support wheel, wherein the rotational ring regions are arranged at a different level with respect to an axis of rotation of the support wheel.

3. The lighting device as claimed in claim 2, wherein the first rotational ring region has at least one phosphor region and at least one reflection region, wherein the reflection region is designed to reflect at least a primary light that can be emitted by the primary light source.

4. The lighting device as claimed in claim 2, wherein the second rotational ring region has at least one filter region and at least one non-filtering region.

5. The lighting device as claimed in claim 1, wherein at least the at least one phosphor region and the at least one filter region are angled relative to one another.

6. The lighting device as claimed in claim 1, wherein the support wheel has a base and a circumferential wall rising from the base, wherein the at least one phosphor region is formed on the wall and the at least one filter region is formed on the base.

7. The lighting device as claimed in claim 6, wherein the support wheel is formed in a cup-shaped fashion and the wall is an outer wall adjacent to an edge of the base.

8. The lighting device as claimed in claim 7, wherein the reflector is at least partly surrounded by the support wheel.

9. The lighting device as claimed in claim 6, wherein the wall is an inner wall rising from a central region of the base.

10. The lighting device as claimed in claim 1, wherein the support wheel is formed at least partly in a strut-shaped fashion.

11. The lighting device as claimed in claim 1, wherein an associated combination of one of the at least one phosphor region and one of the at least one filter region are arranged in a circle sector that is identical with respect to the axis of rotation.

12. The lighting device as claimed in claim 1, wherein the lighting device has a reflector arranged at least partly between the primary light source and the phosphor region which can be irradiated by the primary light source, wherein the reflector is at least partly transmissive to a primary light that can be emitted by the primary light source and is at least partly reflective to a light emitted by the phosphor region, and wherein the at least one optical filter region can be disposed downstream of the reflector.

13. The lighting device as claimed in claim 1, wherein the light source is a semiconductor light source.

14. The lighting device as claimed in claim 1, wherein the lighting device is a vehicle lighting device.

\* \* \* \* \*